United States Patent [19]

Kato et al.

[11] Patent Number: 5,352,590
[45] Date of Patent: Oct. 4, 1994

[54] PROCESS FOR THE PREPARATION OF $^{13}$C-LABELLED COMPOUNDS

[75] Inventors: Nobuo Kato, Tottori; Yoshiyuki Sato, Tokyo; Kunihiko Shibata, Funabashi, all of Japan

[73] Assignee: Tokyo Gas. Co., Ltd., Tokyo, Japan

[21] Appl. No.: 846,478

[22] Filed: Mar. 6, 1992

[30] Foreign Application Priority Data

Mar. 8, 1991 [JP] Japan .................................. 3-067779
Feb. 27, 1992 [JP] Japan .................................. 4-075612

[51] Int. Cl.$^5$ .................................................. C12P 19/02
[52] U.S. Cl. ................................. 435/105; 435/232; 435/233
[58] Field of Search ................. 435/100, 94, 105, 189, 435/232, 233, 234

[56] References Cited

FOREIGN PATENT DOCUMENTS 0220951 5/1987 European Pat. Off. .
62-130692 6/1987 Japan .
8900201 1/1989 World Int. Prop. O. .

OTHER PUBLICATIONS

Methods of Enzymatic Analysis, Third Edition, vol. 6, D-Glucose 6–Phosphate and D-Fructose 6–Phosphate by Gerhard Michal, See Application page 25.
English Abstract of Kaison et al, Japanese Kokia 2-291284, Dec. 1990.
English Abstract of Kajiwara Japanese Kokai 2-111474, Apr. 1990.

Primary Examiner—James C. Housel
Assistant Examiner—Rachel Freed
Attorney, Agent, or Firm—Cushman, Darby & Cushman

[57] ABSTRACT

A process for preparing a $^{13}$C-labelled compound which comprises reacting an alcohol $^{13}$C-labelled carbon source compound and a substrate in the presence of an enzyme system consisting of oxidase belonging to EC1 group and capable of converting the alcohol $^{13}$C-labelled carbon source compound to an aldehyde $^{13}$C-labelled carbon source compound, lyase belonging to EC4 group and capable of synthesizing a carbon-carbon bond and at least one of isomerases belonging to EC5 group and capable of isomerizing substrates to obtain a $^{13}$C-labelled compound specifically labelled with $^{13}$C in a specific carbon position.

14 Claims, 3 Drawing Sheets

○ PROTEIN
● HEXULOSE PHOSPHATE SYNTHASE
▲ PHOSPHOHEXULOISOMERASE

PROCESS FOR THE PREPARATION OF $^{13}$C-LABELLED COMPOUNDS

BACKGROUND OF THE INVENTION

1. Field of the Invention

The present invention relates to a process for preparing $^{13}$C-labelled compounds specifically labelled with $^{13}$C in a specific carbon position.

2. Description of the Prior Art $^{13}$C-labelled fructose 6-phosphate, for example, is known to be prepared by a chemical synthesis process, in which a large number of reaction steps are required in order to obtain $^{13}$C-labelled fructose 6-phosphate labelled with a specifically positioned $^{13}$C because fructose has four asymmetric carbon atoms to provide 16 different optical isomers, resulting in obtaining a product having not so high optical purity.

Japanese Patent Application Laid-Open No. 130692/87 discloses a process for producing isotope labelled biochemicals which comprises cultivating a methylotrophic microorganism in a nutrient medium containing a growth carbon source comprising a $^{13}$C$_1$-compound.

Japanese Patent Application Laid-Open No. 130692/87 discloses a bioconversion process which comprises cultivating a methylotrophic microorganism (or cell extract thereof) in a nutrient medium containing an assimilable C$_n$-compound and a $^{13}$C$_1$-compound to produce an accumulated quantity of $^{13}$C-labelled C$_{n+1}$-condensation product, wherein n is an integer with a value of at least 2.

Japanese Patent Application Laid-Open No. 130692/87 discloses on page 5, right upper column, lines 8-12, that the term "ribulose monophosphate pathway" (RMP) as employed herein refers to the biochemical cycle in which three molecules of formaldehyde are condensed to produce either one molecule of pyruvate or one molecule of dihydroxyacetone phosphate, and further teaches on page 7, left lower column, line 16 to right lower column, line 5, that hexulose 6-phosphate is the product of hexulose phosphate synthase activity and that hexulose phosphate isomerase converts hexulose 6-phosphate to glucose 6-phosphate.

However, Japanese Patent Application Laid-Open No. 130692/87 neither teaches nor suggests process for preparing $^{13}$C-labelled fructose 6-phosphate or $^{13}$C-labelled glucose 6-phosphate specifically labelled with $^{13}$C in a carbon position C-1 from ribose 5-phosphate and $^{13}$C-labelled methanol or $^{13}$C-labelled formaldehyde in the presence of a specific series of enzymes.

Japanese Patent Application Laid-Open No. 130692/87 discloses, in Example, preparation of the exopolysaccharide containing $^{13}$C-glucose as a main constituent by carrying out fermentation using $^{13}$C-methanol as a growth carbon source, resulting in producing $^{13}$C-glucose uniformly labelled with $^{13}$C and in being impossible to obtain $^{13}$C-labelled glucose specifically labelled with $^{13}$C in a carbon position C-1.

The use of $^{13}$C-labelled compounds specifically labelled with $^{13}$C in a specific carbon position in the case of studies on a biological energy metabolism pathway by use of nuclear magnetic resonance apparatus, mass spectrometer, etc. makes it possible to provide useful qualitative and quantitative informations more than in the case of use of compounds uniformly labelled with $^{13}$C, $^{14}$C-labelled compounds, and the like, resulting in that the $^{13}$C-labelled compounds specifically labelled with $^{13}$C in a specific carbon position are applicable to various fields ranging from studies on biological reactions to medical services and development of an industrially advantageous process for the preparation thereof is highly demanded.

For example, fructose 6-phosphate or glucose 6-phosphate is a metabolic intermediate in the glycolitic pathway and is useful for studies of the biological energy metabolism pathway, and $^{13}$C-labelled fructose 6-phosphate or $^{13}$C-labelled glucose 6-phosphate specifically labelled with $^{13}$C in a specific carbon position is preferable on tracing a conversion process of fructose 6-phosphate or glucose 6-phosphate in vivo by use of mass spectrometer, nuclear magnetic resonance apparatus, etc. compared with ones uniformly labelled with $^{13}$C, resulting in that development of an industrially advantageous process for the preparation thereof is highly demanded.

SUMMARY OF THE INVENTION

It is an object of the present invention to provide an industrially advantageous process for the preparation of $^{13}$C-labelled compounds specifically labelled with $^{13}$C in a specific carbon position, for example, $^{13}$C-labelled fructose 6-phosphate or $^{13}$C-labelled glucose 6-phosphate specifically labelled with $^{13}$C in a carbon position C-1.

A first aspect of the present invention provides a process for preparing a $^{13}$C-labelled compound which comprises reacting an alcohol $^{13}$C-labelled carbon source compound and a substrate in the presence of an enzyme system consisting of oxidase belonging to EC1 group and capable of converting the alcohol $^{13}$C-labelled carbon source compound to an aldehyde $^{13}$C-labelled carbon source compound, lyase belonging to EC4 group and capable of synthesizing a carbon-carbon bond and at least one of isomerases belonging to EC5 group and capable of isomerizing substrates to obtain a $^{13}$C-labelled compound specifically labelled with $^{13}$C in a specific carbon position.

A second aspect of the present invention provides a process for preparing a $^{13}$C-labelled compound which comprises isomerizing a substrate in the presence of a first isomerase to form an isomerized substrate, reacting the isomerized substrate in the presence of relase with an aldehyde $^{13}$C-labelled carbon source compound formed by oxidizing an alcohol $^{13}$C-labelled carbon source compound in the presence of oxidase to obtain a condensate specifically labelled with $^{13}$C in a specific carbon position, and isomerizing the condensate in the presence of a second isomerase to obtain a first isomer specifically labelled with $^{13}$C in a specific carbon position, preferably further comprises isomerizing the first isomer in the presence of a third isomerase to obtain a second isomer, preferably said oxidase being used in combination with catalase and hydrogen peroxide.

A preferred embodiment of the first aspect of the present invention provides a process comprising reacting ribose 5-phosphate with $^{13}$C-labelled methanol in the presence of alcohol oxidase and of a formaldehyde-fixing enzyme system obtained from microorganisms growing on methanol and consisting of phosphoriboisomerase, hexulose phosphate synthase and phosphohexuloisomerase to obtain $^{13}$C-labelled fructose 6-phosphate specifically labelled with $^{13}$C in a carbon position C-1.

A preferred embodiment of the second aspect of the present invention provides a process comprising isomerizing ribose 5-phosphate in the presence of phosphoriboisomerase to form riburose 5-phosphate, reacting the riburose 5-phosphate in the presence of hexulose phosphate synthase with $^{13}$C-labelled formaldehyde formed by oxidizing $^{13}$C-labelled methanol in the presence of alcohol oxidase to form $^{13}$C-labelled hexulose 6-phosphate, and isomerizing $^{13}$C-labelled hexulose 6-phosphate in the presence of phosphohexuloisomerase to form $^{13}$C-labelled fructose 6-phosphate specifically labelled with $^{13}$C in a carbon position C-1.

Another preferred embodiment of the present invention provides a process comprising reacting ribose 5-phosphate with $^{13}$C-labelled methanol in the presence of alcohol oxidase and of a formaldehyde-fixing enzyme system obtained from microorganisms growing on methanol and consisting of phosphoriboisomerase, hexulose phosphate synthase, phosphohexuloisomerase and phosphoglucoisomerase to obtain $^{13}$C-labelled glucose 6-phosphate specifically labelled with $^{13}$C in a carbon position C-1.

Another preferred embodiment of the second aspect of the present invention provides a process comprising isomerizing ribose 5-phosphate in the presence of phosphoriboisomerase to form riburose 5-phosphate, reacting the riburose 5-phosphate in the presence of hexulose phosphate synthase with $^{13}$C-labelled formaldehyde formed by oxidizing $^{13}$C-labelled methanol in the presence of alcohol oxidase to form $^{13}$C-labelled hexulose 6-phosphate, isomerizing $^{13}$C-labelled hexulose 6-phosphate in the presence of phosphohexuloisomerase to form $^{13}$C-labelled fructose 6-phosphate specifically labelled with $^{13}$C in a carbon position C-1, and isomerizing $^{13}$C-labelled fructose 6-phosphate in the presence of phosphoglucoisomerase to form $^{13}$C-labelled glucose 6-phosphate specifically labelled with $^{13}$C in a carbon position C-1.

A third aspect of the present invention provides a process for preparing a $^{13}$C-labelled compound which comprises reacting a substrate and an aldehyde $^{13}$C-labelled carbon source compound in the presence of an enzyme system consisting of lyase belonging to EC4 group and capable of synthesizing a carbon-carbon bond and at least one of isomerases capable of isomerizing substrates to obtain a $^{13}$C-labelled compound specifically labelled with $^{13}$C in a specific carbon position.

A fourth aspect of the present invention provides a process for preparing a $^{13}$C-labelled compound which comprises isomerizing a substrate in the presence of a first isomerase to form an isomerized substrate, reacting the isomerized substrate in the presence of lyase with an aldehyde $^{13}$C-labelled carbon source compound to obtain a condensate specifically labelled with $^{13}$C in a specific carbon position, and isomerizing the condensate in the presence of a second isomerase to obtain a first isomer specifically labelled with $^{13}$C in a specific carbon position, preferably further comprising isomerizing the first isomer in the presence of a third isomerase to form a second isomer.

A preferred embodiment of the third aspect of the present invention provides a process which comprises reacting ribose 5-phosphate with $^{13}$C-labelled formaldehyde in the presence of a formaldehyde-fixing enzyme system obtained from a microorganism growing on methanol and consisting of phosphoriboisomerase, hexulose phosphate synthase and phosphohexuloisomerase to obtain $^{13}$C-labelled fructose 6-phosphate specifically labelled with $^{13}$C in a carbon position C-1.

Another preferred embodiment of the third aspect of the present invention provides a process which comprises reacting ribose 5-phosphate with $^{13}$C-labelled formaldehyde in the presence of a formaldehyde-fixing enzyme system obtained from a microorganism growing on methanol and consisting of phosphoriboisomerase, hexulose phosphate synthase, phosphohexuloisomerase and phosphoglucoisomerase to obtain $^{13}$C-labelled glucose 6-phosphate specifically labelled with $^{13}$C in a carbon position C-1.

A preferred embodiment of the fourth aspect of the present invention provides a process which comprises isomerizing ribose 5-phosphate in the presence of phosphoriboisomerase to form riburose 5-phosphate, reacting the riburose 5-phosphate with $^{13}$C-labelled formaldehyde in the presence of hexulose phosphate synthase to form $^{13}$C-labelled hexulose 6-phosphate, and isomerizing $^{13}$C-labelled hexulose 6-phosphate in the presence of phosphohexuloisomerase to form $^{13}$C-labelled fructose 6-phosphate specifically labelled with $^{13}$C in a carbon position C-1.

Another preferred embodiment of the fourth aspect of the present invention provides a process which comprises isomerizing ribose 5-phosphate in the presence of phosphoriboisomerase to form riburose 5-phosphate, reacting the riburose 5-phosphate with $^{13}$C-labelled formaldehyde in the presence of hexulose phosphate synthase to form $^{13}$C-labelled hexulose 6-phosphate, isomerizing $^{13}$C-labelled hexulose 6-phosphate in the presence of phosphohexuloisomerase to form $^{13}$C-labelled fructose 6-phosphate, and isomerizing $^{13}$C-labelled fructose 6-phosphate in the presence of phosphoglucoisomerase to form $^{13}$C-labelled glucose 6-phosphate specifically labelled with $^{13}$C in a carbon position C-1.

In the aforementioned preferred embodiments of the first to fourth aspects of the present invention, preferably hexulose phosphate synthase and phosphohexuloisomerase are prepared by a process which comprises incubating and growing *Methylomonas aminofaciens* 77a strain with a liquid medium containing methanol as a sole carbon source to obtain a cell-free extract, and separating and purifying the cell-free extract.

DETAILED DESCRIPTION OF THE INVENTION

Examples of oxidase belonging to EC1 group and capable of converting an alcohol $^{13}$C-labelled carbon source compound to an aldehyde $^{13}$C-labelled carbon source compound may include, as ones capable of converting $^{13}$C-labelled methanol to $^{13}$C-labelled formaldehyde, alcohol dehydrogenase, alcohol oxidase, and the like.

The oxidase may preferably be used in combination with catalase and hydrogen peroxide.

Examples of lyase belonging to EC4 group and capable of synthesizing a carbon-carbon bond in the present invention may include hexulose phosphate synthase, phosphoribosylaminoimidazole carboxylase, phosphoenol pyruvate carboxykinase, ribulose bisphosphate carboxylase, ketotetrose phosphate aldolase, threonine aldolase, fructose bisphosphate aldolase, phospho-2-keto-3-deoxy-gluconate aldolase, L-fuculose phosphate aldolase, 2-keto-3-deoxy-L-pentonate aldolase, L-rhamnulose-1-phosphate aldolase, 2-keto-3-deoxy-D-glucarate aldolase, 6-phospho-2-keto-3-deoxy-galactonate aldolase, fructose-6-phosphate phosphoketolase, 3-deoxy-D-mannooctulophosphate aldolase, phenylserine aldolase, 2-keto-3-deoxy-D-pentonate aldolase, phospho-5-keto-2-deoxy-gluconate aldolase, 17α-hydroxyprogesterone aldolase, 2-oxo-4-hydroxyglutarate aldolase, trimethylamine-oxide aldolase, isocitrate lyase, malate synthetase, N-acetylneuraminate lyase, citrate lyase, citrate synthase, 3-hydroxyaspartate aldolase, 4-hydroxy-2-oxoglutarate aldolase, N-acetylneutaminate synthase, malyl-CoA lyase, 3-hydroxy-3-isohexenylglutaryl-CoA lyase, methylacetate synthase, deoxyribodipyrimidine photolyase, fumarate hydratase, carbonate dihydratase, aconitate hydratase, cystathionine β-synthase, lactoyl-glutathione lyase, and the like, preferably hexulose phosphate synthase, ribulose bisphosphate carboxylase, ketotetrose phosphate aldolase, fructose bisphosphate aldolase, L-fuculose phosphate aldolase, 2-keto-3-deoxy-D-glucarate aldolase, 6-phospho-2-keto-3-deoxy-galactonate aldolase, 3-deoxy-D-mannooctulo-phosphate aldolase, phospho-5-keto-2-deoxy-gluconate aldolase and 2-oxo-4-hydroxyglutarate, because one of the substrates is easily available as a $^{13}$C-labelled carbon source in the case of synthesis of $^{13}$C-labelled compound by a condensation reaction.

Examples of the isomerase belonging to EC5 group and capable of isomerizing the substrate may include phosphohexuloisomerase, phosphoriboisomerase, maleate isomerase, maleylacetoacetate isomerase, retinal isomerase, maleylpyruvate isomerase, linoleate isomerase, furylfuramide isomerase, triosephosphate isomerase, arabinose isomerase, xylose isomerase, mannose isomerase, mannosephosphate isomerase, glucosaminephosphate isomerase, glucuronate isomerase, arabinosephosphate isomerase, L-rhamnose isomerase, D-lyxase ketol-isomerase, steroid isomerase, isopentenyldiphosphate isomerase, prostaglandin isomerase, protein disulfide-isomerase, hydroperoxide isomerase, ribulosephosphate 3-epimerase, UDP glucose 4-epimerase, aldose 1-epimerase, L-ribulosephosphate 4-epimerase, UDP arabinose 4-epimerase, UDP glucuronate 4-epimerase, UDP acetylglucosamine 4-epimerase, acylglucosamine 2-epimerase, phosphoglucoisomerase, and the like, preferably, from the standpoint of specificity to the substrate in the preparation of sugar by isomerization reaction, may include phosphohexuloisomerase, phosphoriboisomerase, arabnose isomerase, xylose isomerase, annose isomerase, mannosephosphate isomerase, and phosphoglucoisomerase.

The formaldehyde-fixing enzyme system used in the present invention may preferably include phosphoriboisomerase, hexulose phosphate synthase and phosphohexuloisomerase, or further phosphoglucoisomerase.

The phosphoriboisomerase used in the present invention isomerizes ribose 5-phosphate to ribulose 5-phosphate and is available from Sigma Biochemicals.

The hexulose phosphate synthase in the present invention is used for forming $^{13}$C-labelled hexulose 6-phosphate by a reaction between ribulose 5-phosphate and $^{13}$C-labelled formaldehyde, and may be obtained by a process which comprises culturing microorganisms such as bacteria strictly growing on methanol, for example, *Methylomonas aminofaciens* 77a strain deposited as FERM P-12019, *Methylococcus capsulatus* strain obtained as strain ATCC 19069 and the like, by use of methanol, methane, etc., and separating from reaction products by use of various chromatography apparatuses.

Examples of other microorganisms than the above may include *Methylomonas methanica, Methylomonas agile* and *M. rosaceous, Methylomonas rubrum*, Methylomonas GB3 and GB8, *Methylococcus minimus, Methylococcus ucrainicus* and *M. thermophilus, Methylobacter capsulatus, Methylobacter bovis* and *M. vinelandii, Methylobacter chroococcum*, Pseudomonas W1, Organism 4B6, Pseudomonas C, Pseudomonas W6, Organism C2A1, Organisms W3A1 and W6A, Methylomonas M15, *Methylophilus methylotrophus*, Organism L3, Arthrobacter, Bacillus sp. PM6 and S2A1, *Arthrobacter globiformis*, Streptomyces sp. 239, *Pseudomonas oleovorans*, Organisms MB53, 55, 56, 57, 58, 59 and 60, *Brevibacterium fuscum* 24, *Mycobacterium vaccae* 10, Arthrobacter P1, Nocardia 239, and the like.

The phosphohexuloisomerase in the present invention is used for isomerizing $^{13}$C-labelled hexulose 6-phosphate to form $^{13}$C-labelled fructose 6-phosphate, and may be obtained by a process which comprises culturing, for example, *Methylomonas aminofaciens* 77a strain deposited as FERM P-12019 by use of methanol to form a cell-free extract, followed by purifying and separating.

A cell-free extract prepared by incubating and culturing *Methylomonas aminofaciens* 77a strain deposited as FERM P-12019 with a liquid medium containing methanol as a sole carbon source may also be used as the formaldehyde-fixing enzyme system. Since the cell-free extract contains phosphoglucoisomerase in addition to phosphoriboisomerase, hexulose phosphate synthase and phosphohexuloisomerase, resulting fructose 6-phosphate may partly be isomerized to form glucose 6-phosphate.

The strain used in the present invention may be cultured by a process which comprises adding methanol in such an amount as not to inhibit growth of the strain into a solution containing mineral nutrients in a minimum amount necessary for growing, and incubating at around 30° C. providing oxygen in a sufficient amount by agitation, air blowing, etc.

The phosphoglucoisomerase in the present invention isomerizes $^{13}$C-labelled fructose 6-phosphate to form $^{13}$C-labelled glucose 6-phosphate and is available, for example, from Sigma Biochemicals as Type III.

The substrate used in the present invention may include biological compounds, more specifically phosphoenolpyruvic acid, 3-phosphoglycerate, dihydroxyacetone phosphate, acetaldehyde, glyceraldehyde 3-phosphate, erythrose 4-phosphate, tartronate-semialdehyde, arabinose, benzaldehyde, pyruvic acid, dimethylamine, glyoxylic acid, succinic acid, acetyl-coenzyme A, N-acetylmannosamine, propionyl-CoA, fumaric acid, riburose 5-phosphate, ribose 5-phosphate, and the like, preferably phosphoenolpyruvic acid, 3-phosphoglycerate, acetaldehyde, glyceraldehyde 3-phosphate, pyruvic acid, riburose 5-phosphate, and ribose 5-phosphate, more preferably ribose 5-phosphate which is easily available as a starting material for the biological synthesis of hexose 6-phosphate such as fructose 6-phosphate and glucose 6-phosphate.

The $^{13}$C-labelled carbon source compound in the present invention may include compounds easily labellable with $^{13}$C by chemical synthesis, and specifically, $^{13}$C-labelled respectively, carbon dioxide, methanol, formaldehyde, acetaldehyde, dihydroxyacetone phosphate, pyruvic acid, phosphoenolpyruvic acid, L-lactoaldehyde, glycolaldehyde, malonate semialdehyde, glyoxilic acid, succinic acid, acetyl-CoA, acetic acid, oxaloacetic acid and the like, preferably carbon dioxide, methanol, formaldehyde, acetaldehyde, pyruvic acid, acetic acid and oxaloacetic acid.

The $^{13}$C-labelled methanol used in the present invention may be available, for example, from MSD Isotope Co., Ltd. with a $^{13}$C concentration of 99 wt %.

The $^{13}$C-labelled formaldehyde used in the present invention may include commercially available ones such as $^{13}$C-labelled formaldehyde having a $^{13}$C concentration of 99 wt % and marketed by MSD Isotope Co., Ltd.

The $^{13}$C-labelled compound specifically labelled with $^{13}$C in a specific carbon position and prepared according to the present invention may include biological compounds, specifically oxaloacetate, riburose 1,5-diphosphate, hexulose 6-phosphate, erythrulose 1-phosphate, threonine, fructose 1,6-diphosphate, 6-phospho-2-keto-3-deoxygluconic acid, 7-phospho-2-keto-3-deoxyarabinoheptinate, L-fuculose 1-phosphate, 2-keto-3-deoxypentnate, rhamnulose 1-phosphate, 2-keto-3-deoxyglucaric acid, erythrophenylserine, 6-phospho-5-keto-2-deoxygluconic acid, 2-oxo-4-hydroxyglutaric acid, trimethylalanine N-oxide, isocitric acid, malic acid, N-acetylneuraminic acid, citric acid, fructose 6-phosphate, riburose 5-phosphate, glucose 6-phosphate and the like, preferably riburose 1,5-diphosphate, hexulose 6-phosphate, erythrulose 1-phosphate, threonine, fructose 1,6-diphosphate, citric acid, fructose 6-phosphate, riburose 5-phosphate, and glucose 6-phosphate. Of these, fructose 6-phosphate and glucose 6-phosphate are particularly preferable, because the former is an intermediate in vivo, the latter is metabolized in the glycolytic pathway or pentose phosphate cycle, and both are effective when applied to organism.

The present invention makes it possible to prepare $^{13}$C-labelled compounds specifically labelled with $^{13}$C in a specific position, for example, $^{13}$C-labelled fructose 6-phosphate or $^{13}$C-labelled glucose 6-phosphate specifically labelled with $^{13}$C in a carbon position C-1 with extremely high optical purity and at high selectivity and yield in one or few steps without needing a large number of reaction steps as in the conventional chemical synthesis process.

The present invention makes it possible to provide an industrially advantageous process for preparing $^{13}$C-labelled compounds specifically labelled with $^{13}$C in a specific carbon position, for example, $^{13}$C-labelled fructose 6-phosphate and $^{13}$C-labelled glucose 6-phosphate specifically labelled with $^{13}$C in a carbon position C-1, which are metabolic intermediates in the glycolitic pathway and are useful for studies of the biological energy metabolism pathway, which are capable of providing useful qualitative and quantitative informations compared with compounds uniformly labelled with $^{13}$C or the like, and which are applicable to various fields ranging from studies on biological reactions to medical services.

The present invention will be explained more in detail by the following Examples, in which such experiments as in the determination of $^{13}$C-labelled fructose 6-phosphate, separation and purification of $^{13}$C-labelled fructose 6-phosphate, determination of activity of phosphohexuloisomerase and phosphoglucoisomerase, etc. were carried out methanol, formaldehyde, fructose 6-phosphate, glucose 6-phosphate and the like, instead of using the corresponding $^{13}$C-labelled compounds so long as the use of the former is expected to provide the same results as in the latter.

EXAMPLE 1

A test tube was charged with a reaction mixture shown in the following Table 1 to incubate at 30° C. for 30 minutes.

TABLE 1

| Reaction mixture | |
|---|---|
| Reagent | Final conc. |
| $^{13}$C-methanol | 100 mM |
| ribose 5-phosphate | 75 mM |
| alcohol oxidase | 10 U/ml |
| phosphoriboisomerase | 10 U/ml |
| 3-hexulose phosphate synthase | 5 U/ml |
| phosphohexuloisomerase | 5 U/ml |
| phosphoglucoisomerase | 5 U/ml |
| magnesium chloride | 5 mM |
| potassium phosphate buffer solution (pH 7.5) | 50 mM | at 30° C.

In Table 1, $^{13}$C-methanol marketed by MSD Co., Ltd. with a $^{13}$C concentration of 99%, ribose 5-phosphate marketed by Kyowa Hakko Co., Ltd., alcohol oxidase marketed by Toyoboseki Co., Ltd. as III and phosphoisomerase marketed by Sigma Biochemicals as Type III were used respectively.

In Table 1, hexulose phosphate synthase and phosphohexuloisomerase were prepared by incubating and culturing *Methylomonas aminofaciens* 77a strain deposited as FERM P-12019 with a liquid medium containing methanol as a sole carbon source to obtain a cell-free extract, and separating and purifying the cell-free extract by use of various chromatography apparatuses.

Details of the above culture and separation are explained in the following.

The above *Methylomonas aminofaciens* 77a was cultured at 30° C. for 72 hours in a liquid medium containing methanol as a sole carbon source as shown in Table 2.

TABLE 2

| Composition | (g) | |
|---|---|---|
| NaNO$_3$ | 2.0 | |
| (NH$_4$)$_2$SO$_4$ | 2.0 | |
| K$_2$HPO$_4$ | 2.0 | |
| KH$_2$PO$_4$ | 1.0 | |
| MgSO$_4$.7H$_2$O | 0.2 | |
| yeast extract | 2.0 | |
| ★ VIT2 | 1.0 ml | |
| ☆ ME2 | 10.0 ml | |
| deionized water | 1.0 l | |
| methanol | 10.0 ml | pH 7.0 |
| ★ VIT2 (vitamin mixed solution) | | |
| Ca-panthonate | 400 mg | |
| inositol | 200 mg | |
| niacin | 400 mg | |

TABLE 2-continued

| | |
|---|---|
| p-aminobenzoate | 200 mg |
| pyridoxine | 400 mg |
| thiamine HCl | 400 mg |
| biotin | 2 mg |
| vitamin $B_{12}$ | 0.5 mg |
| Total volume | 1.0 l |

☆ ME2 (metal salts mixed solution)

| | |
|---|---|
| $CaCl_2.2H_2O$ | 400 mg |
| $H_3BO_3$ | 500 mg |
| $CuSO_4.5H_2O$ | 40 mg |
| KI | 100 mg |
| $FeSO_4.7H_2O$ | 200 mg |
| $MnSO_4.4-7H_2O$ | 400 mg |
| $ZnSO_4.7H_2O$ | 400 mg |
| $Na_2MoO_4.2H_2O$ | 100 mg |
| conc. HCl | 10 ml |
| Total volume | 1.0 l |

Figure 1:
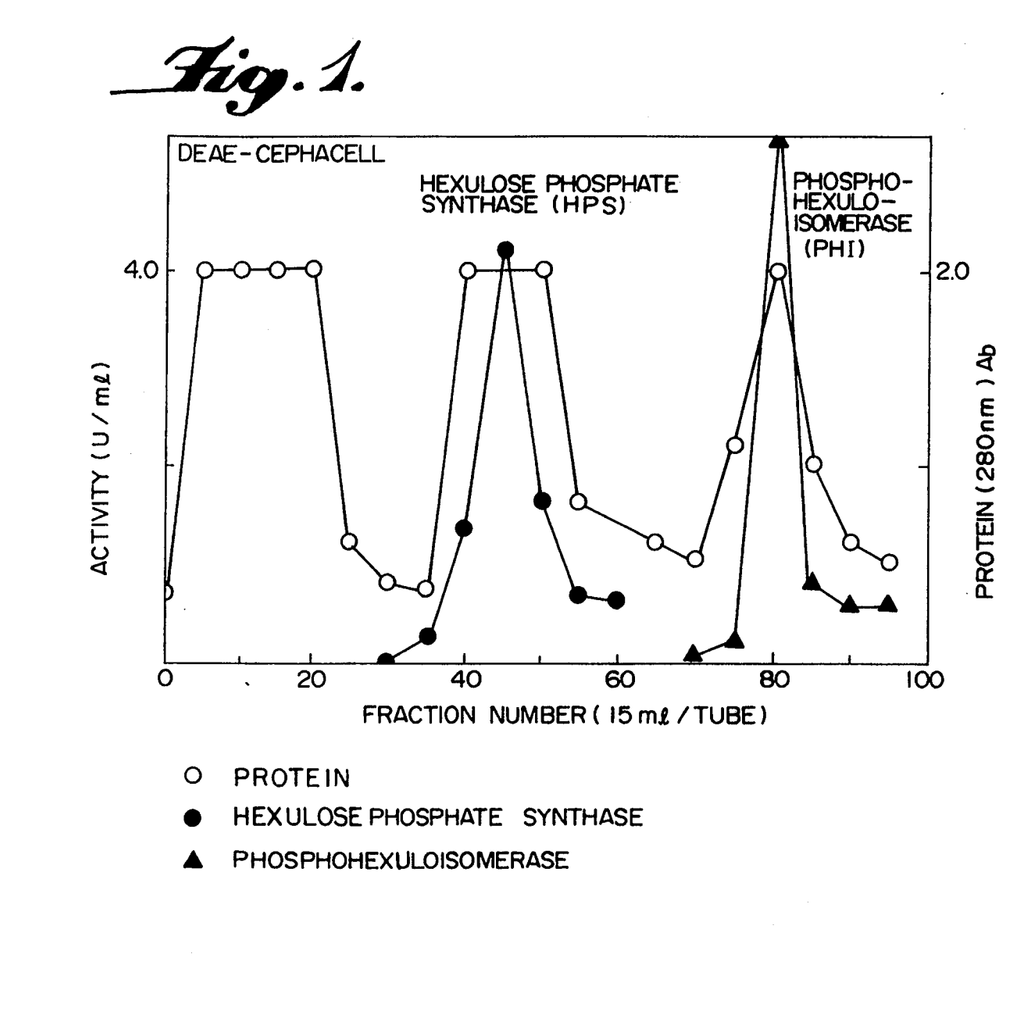
FIG. 1 is a graph showing results of separation and purification of hexulose phosphate synthase and phosphohexuloisomerase from a cell-free extract of *Methylomonas aminofaciens* 77a strain in the present invention.

Hexulose phosphate synthase and phosphohexuloisomerase were fractionated from a cell-free extract of the above Methylomonas aminofaciens 77a by use of DEAE-cephacell column chromatography, and the resulting enzymes were further subjected to fractionation by the above chromatography with the result shown in FIG. 1 and Table 3.

Table 3 shows the results of partial purification of hexulose phosphate synthase and phosphohexuloisomerase.

TABLE 3

Hexulose phosphate synthase (HPS):

| Purification method | Total protein (mg) | Total activity (U) | Specific activity (U/mg) |
|---|---|---|---|
| cell-free extract | 1242 | 6458 | 5.2 |
| After DEAE-cephacell column chromatography treatment | 72.2 | 374.4 | 5.2 |

*Phosphoglucoisomerase: Total activity 0.82 U (0.2%)

Phosphohexuloisomerase (PHI):

| Purification method | Total protein (mg) | Total activity (U) | Specific activity (U/mg) |
|---|---|---|---|
| cell-free extract | 1242 | 290 | 0.24 |
| After DEAE-cephacell column chromatography treatment | 606.5 | 22670 | 37.4 |

*Phosphoglucoisomerase: Total activity 0.82 U (0.2%)

The preparations of the resulting hexulose phosphate synthase and phosphohexuloisomerase contained 0.2% and 1.7% of phosphoglucoisomerase as the total activity (U) respectively.

The above DEAE-cephacell column chromatography treatment was carried out as follows. Into a column (5×20 cm) buffered with 10 mM of Tris-HCl (pH 8.2) was introduced, followed by washing with 2 liter of the above buffer solution, and by increasing a concentration of the buffer solution for eluting the enzymes. As shown in FIG. 1, hexulose phosphate synthase was eluted by 100 mM of Tris-HCl (pH 8.2) and phosphohexuloisomerase was eluted by a mixture of 100 mM of Tris-HCl (pH 8.2) and 100 mM NaCl.

In Table 1, phosphoglucoisomerase marketed by Sigma Biochemicals as Type III was used.

As the result of the above culture, 63 mM of $^{13}C$-labelled glucose 6-phosphate specifically labelled with $^{13}C$ in a specific carbon position C-1 was obtained with an yield of 63% based on $^{13}C$-methanol, and 18 mM of $^{13}C$-labelled fructose 6-phosphate specifically labelled with $^{13}C$ in a specific carbon position C-1 was obtained with an yield of 13% based on $^{13}C$-methanol.

Determination of $^{13}C$-labelled glucose 6-phosphate (G6P)

$^{13}C$-labelled glucose 6-phosphate was determined according to the enzymatic process, which is known as the Michael et al. process, by use of a reaction mixture as shown in Table 4 and glucose 6-phosphate dehydrogenase.

TABLE 4

| Composition | Amount (ml) |
|---|---|
| 0.4M triethanolamine (pH 7.0) | 0.5 |
| 0.5M $MgCl_2$ | 0.01 |
| 24 mM NADP | 0.01 |
| Sample | 0.5 |
| 11.67 U/ml G6PDH | 0.015 |

Determination procedures
1. A blank test was carried out by adding 0.5 ml of distilled water in place of the sample.
2. A zero point was determined prior to adding enzymes.
3. Glucose 6-phosphate dehydrogenase was then added, an increased absorbance at 340 nm was measured with time, and at the time when the absorbance was saturated, a difference in the absorbance from the zero point was recorded as $\Delta A_{340/G6P}$. The concentration (mM) of glucose 6-phosphate was determined as X according to the following equation:

$$X \text{ (mM)} = \frac{\Delta A_{340/G6P}}{6.22} \times \frac{a}{b} \times \text{(degree of dilution for sample)}$$

where "6.22" is a molecular extinction coefficient (μmol/ml) at 340 nm for nicotinamide adenine dinucleotide phosphate (NADPH, reduced type), "a" is a volume (ml) of the reaction mixture and "b" is a volume (ml) of the sample.

Separation and purification of $^{13}C$-labelled fructose 6-phosphate (F6P)

After the completion of culturing, the resulting reaction mixture was added to DEAE-TOYOPEARL (ion exchange chromatography, trade name, marketed by Toso Co., Ltd.) column, followed by carrying out a step gradient process to pass through successively exchanging the following three different moving phases:

| | | | |
|---|---|---|---|
| (1) | 0.02M | $NH_4HCO_3$ | 100 ml |
| (2) | 0.05M | $NH_4HCO_3$ | 150 ml |
| (3) | 0.2M | $NH_4HCO_3$ | 50 ml | and to collect $^{13}C$-labelled F6P fraction.

Figure 3A:
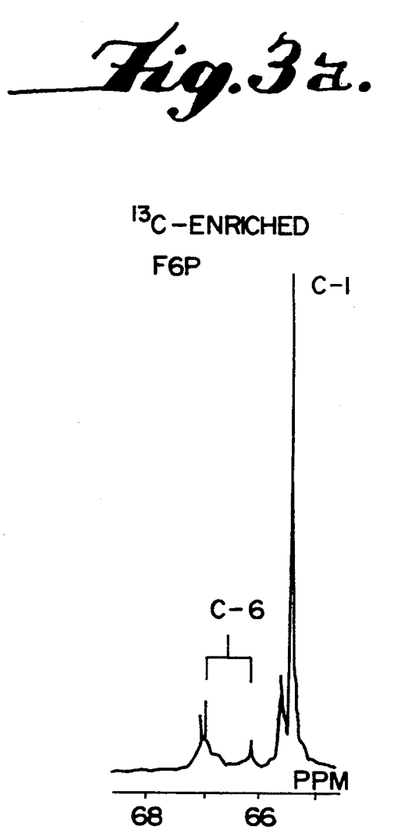
FIG. 3 is a NMR chart showing the results of $^{13}$C-NMR analysis of $^{13}$C-labelled fructose 6-phosphate obtained in the present invention.
Figure 3B:
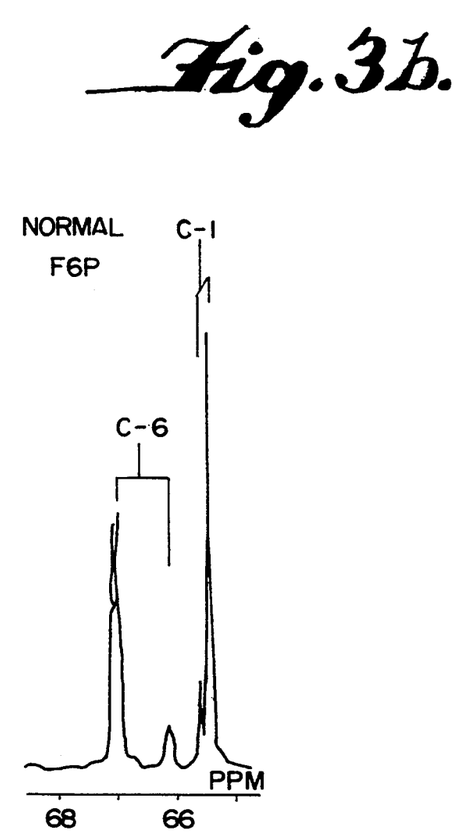

The $^{13}C$-labelled fructose 6-phosphate fractions as shown in FIG. 3 as fractions 14–19 were collected and added to MUROMAC (ion exchange resin, trade name, marketed by Muromachi Chemical Co., Ltd.) 50 W×8 ($H^+$ type) column, followed by passing the $^{13}C$-labelled fructose 6-phosphate through the column by use of distilled water as a moving phase for adsorbing impurities onto the column. The eluent containing the recovered $^{13}C$-labelled fructose 6-phosphate was concentrated by an evaporator, followed by adding to a MUROMAC (ion exchange resin, trade name, marketed by Muromachi Chemical Co., Ltd.) 50 W×8 ($Na^+$ type) column, passing it through the column by use of distilled water as a moving phase, adsorbing impurities onto the column, and by concentrating the resulting eluent to obtain sodium $^{13}$C-labelled fructose 6-phosphate.

Figure 2:
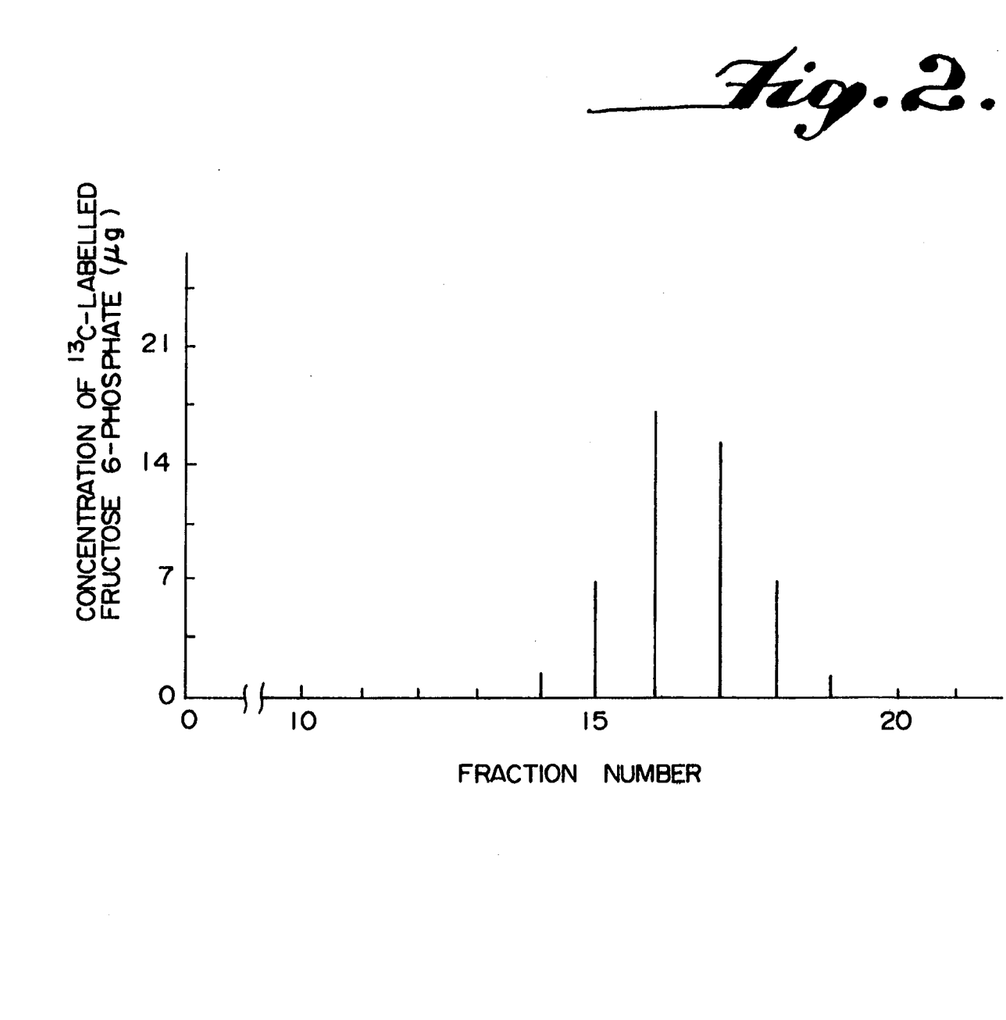
FIG. 2 is a graph showing an elution pattern of a column chromatography for the separation and purification of $^{13}$C-labelled fructose 6-phosphate used in the present invention.

An elution pattern according to a column chromatography by use of DEAE-TOYOPEARL (ion exchange chromatography, trade name, marketed by Toso Co., Ltd.) filler is shown in FIG. 2. Percentage of recovery was about 54% and purity was about 64%.

$^{13}$C-NMR analysis of $^{13}$C-labelled fructose 6-phosphate

Fructose 6-phosphate prepared by an enzymatic synthesis by use of H$^{13}$CHO as a substrate was mixed with fructose 6-phosphate marketed by Sigma Biochemicals to form a mixture containing 10% $^{13}$C, which was taken as $^{13}$C-enriched fructose 6-phosphate, and one marketed by Sigma Biochemicals was taken as pure fructose 6-phosphate. Both was subjected to $^{13}$C-NMR analysis respectively. FIG. 3 shows the results of comparison between a carbon position C-1 and a carbon position C-6 in fructose 6-phosphate. FIG. 3 further shows that a peak ratio C-1/C-6 in the above $^{13}$C-enriched fructose 6-phosphate is about 10 times that in the above pure fructose 6-phosphate. This shows that $^{13}$C-labelled fructose 6-phosphate obtained by the enzymatic synthesis process is specifically labelled with $^{13}$C in the carbon position C-1.

Determination of $^{13}$C-labelled fructose 6-phosphate (F6P)

$^{13}$C-labelled fructose 6-phosphate was determined according to the enzymatic process, which is known as the Michael et al. process, by use of a reaction mixture as shown in Table 5 as well as phosphoglucoisomerase (PGI) and glucose 6-phosphate dehydrogenase (G6PDH) (see Methods in Enzymatic Analysis 3rd Vol. 6, Verlag Chemie GmbH Weinheim, p 191–198).

TABLE 5

| Composition | Amount (ml) |
| --- | --- |
| 0.4M triethanolamine (pH 7.0) | 0.5 |
| 0.5M MgCl$_2$ | 0.01 |
| 24 mM NADP | 0.01 |
| Sample | 0.5 |
| 11.67 U/ml G6PDH | 0.015 |
| 250.0 U/ml PGI | 0.01 |
| Total volume | 1.045 |

Determination procedures:

1. A blank test was carried out by adding 0.5 ml of distilled water in place of the sample.
2. A zero point was determined prior to adding enzymes.
3. Glucose 6-phosphate dehydrogenase (G6PDH) and phosphoglucoisomerase were successively added, an increased absorbance at 340 nm was measured with time, and at the time when the absorbance was saturated, a difference in the absorbance from the zero point was recorded as $\Delta A_{340/F6P}$.

When both glucose 6-phosphate and fructose 6-phosphate are present, G6PDH only was first added to determine $\Delta A_{340/G6P}$ in the same manner as the above, followed by adding phosphoglucoisomerase to determine $\Delta A_{340/F6P}$. The concentration (mM) of glucose 6-phosphate was determined as X according to the following equation:

$$X \text{ (mM)} = \frac{\Delta A_{340/F6P}}{6.22} \times \frac{a}{b} \times \text{(degree of dilution for sample)}$$

where "6.22" is a molecular extinction coefficient ($\mu$mol/ml) at 340 nm for nicotinamide adenine dinucleotide phosphate (NADPH, reduced type), "a" is a volume (ml) of the reaction mixture and "b" is a volume (ml) of the sample.

Determination of riburose 5-phosphate (R5P) was carried out by fluoroglycine-acetic acid process. Determination of activity of hexulose phosphate synthase (HPS) was carried out by use of a reaction mixture shown in Table 6.

TABLE 6

| Composition | Amounts (ml) | Final concentration (mM) | |
| --- | --- | --- | --- |
| H$_2$O | 0.2 | | |
| KPB (0.5M pH 7.5) | 0.05 | 50 | |
| MgCl$_2$ (50 mM) | 0.05 | 5 | |
| R5P (50 mM) | 0.05 | 5 | |
| PR1 (100 U/ml) | 0.05 | 10 | |
| hexulose phosphate synthase | 0.05 | | preincubation |
| HCHO (20 mM) | 0.05 | 2 | 30° C., 30 min |

Determination procedures:

1. A blank test was carried out by adding distilled water in place of ribose 5-phosphate.
2. HCHO was added to start reacting, and 5 minutes after 1N-HCl was added to stop the reaction.
3. To 0.1 ml of the resulting reaction mixture was added 1.9 ml of distilled water to be diluted by 20 times, followed by adding 2.0 ml of Nash reagent, leaving to stand at 30° C. for 30 minutes for coloring.
4. An absorbance was measured at 410 nm and concentration of HCHO was determined from a calibration curve. Activity was determined according to an equation shown hereinbelow.

The above Nash reagent consists of 15 g of ammonium acetate, 0.3 ml of acetic acid and 0.2 ml of acetylacetone. The Nash reagent was dissolved in distilled water to form a 100 ml aqueous solution.

The above calibration curve was prepared by use of HCHO of 0.04, 0.08, 0.12, 0.16 and 0.2 mM respectively.

Activity was determined according to the following equation:

Activity
$(U/ml)=\{(A-B)\times C\}\times D\times(1/E)\times(1/F)\times(0.6/0.5)\times 0.5$ where A is a concentration (mM) of HCHO in a blank test, B is a concentration (mM) of HCHO in the reaction mixture, C is a degree of dilution for an enzyme used, D is a degree of dilution for a reaction mixture in the Nash process, E is a volume (ml) of an enzyme used in the reaction, F is a reaction time, "0.6/0.5" means a constant for determining a concentration of HCHO prior to adding HCl, and "0.5" means a volume (ml) of the reaction mixture.

Activity of phosphohexuloisomerase was determined by use of a reaction mixture shown in Table 7.

TABLE 7

| Composition | Amounts (ml) | Final concentration (mM) | |
|---|---|---|---|
| H₂O | (0.12) | | |
| KPB (0.1M pH 7.5) | 0.5 | 50 | |
| MgCl₂ (75 mM) | 0.033 | 2.5 | |
| R5P (75 mM) | 0.033 | 2.5 | |
| PRI (666.7 U/ml) | 0.02 | 13.3 | U/ml |
| PGI (500 U/ml) | 0.02 | 10 | U/ml |
| G6PDH (116.7 U/ml) | 0.01 | 1.2 | U/ml |
| *(HPS or H₂O) | (0.9) | about 1.0 | U/ml |
| NADP (15 mM) | 0.033 | 0.5 | |
| phosphohexuloisomerase | 0.1 | | preincubation |
| HCHO (60 mM) | 0.05 | 3 | 30° C., 30 min |

Determination procedures:
1. A standard cuvette was prepared by adding distilled water in place of HCHO.
2. HCHO was added to start reacting. Increase in absorbance for NADPH at 340 nm was measured by use of a black cell.
3. Activity was determined by measuring a slope in the range where absorbance linearly increases as $\Delta A_{340\ nm/min}$ and by introducing the value of the slope into the following equation.

* In Table 7, since activity of hexulose phosphate synthase (HPS) varies depending on purification conditions, it was added in such an amount that the final concentration or activity may be about 1.0 U/ml as shown in the above reaction mixture. Distilled water was also added in such an amount that a total volume of the reaction mixture may be 1.0 ml.

On determining activities of the enzymes used in the present invention, addition of PHS was replaced by addition of 0.9 ml of distilled water.

As mentioned above, activity was determined according to the following equation:

$$\text{Activity }(U/ml) = (A/6.22) \times (1/B) \times C \times D$$

where A is $\Delta A_{340\ nm/min}$, B is a volume of an enzyme used in the reaction, C is a degree of dilution of an enzyme used, D is a volume of a reaction mixture, and "6.22" is a molecular extinction coefficient ($\mu$mol/ml) at 340 nm for NADPH.

Measurement of the activity of phosphoglucoisomerase was carried out by use of a reaction mixture shown in Table 8.

TABLE 8

| Composition | Amounts (ml) | Final concentration or activity (mM) | |
|---|---|---|---|
| H₂O | 0.283 | | |
| KPB (0.1M pH 7.5) | 0.5 | 50 | |
| MgCl₂ (75 mM) | 0.033 | 2.5 | |
| G6PDH (116.7 U/ml) | 0.01 | 1.2 | (U/ml) |
| NADP (15 mM) | 0.003 | 0.5 | |
| phosphogluco-isomerase | 0.1 | | preincubation |
| F6P (60 mM) | 0.05 | 3 | 30° C., 30 min |

Determination procedures
1. A standard cuvette was prepared by adding distilled water in place of fructose 6-phosphate.
2. Fructose 6-phosphate was added to start reacting. Increase in absorbance for NADPH at 340 nm was measured by use of a black cell.
3. Activity was determined by measuring a slope in the range where absorbance linearly increases as $\Delta A_{340\ nm/min}$ and by introducing the value of the slope into the following equation:

$$\text{Activity }(U/ml) = (A/6.22) \times (1/B) \times C \times D$$

where A is $\Delta A_{340\ nm/min}$, B is a volume of an enzyme used in the reaction, C is a degree of dilution of an enzyme used, D is a volume of a reaction mixture, and "6.22" is a molecular extinction coefficient ($\mu$mol/ml) at 340 nm for NADPH.

EXAMPLE 2

Procedures of Example 1 were repeated except that a reaction mixture shown in Table 9 in place of the reaction mixture shown in Table 1 as in Example 1 was used with the results that 31 mM of $^{13}$C-labelled glucose 6-phosphate specifically labelled with $^{13}$C in a carbon position C-1 with an yield of 62% based on H$^{13}$CHO and 8 mM of $^{13}$C-labelled fructose 6-phosphate specifically labelled with $^{13}$C in a carbon position C-1 with an yield of 16% based on H$^{13}$CHO.

In Table 9, $^{13}$C-labelled formaldehyde was used in the form of a 20% aqueous formalin-$^{13}$C from $^{13}$C-labelled formaldehyde containing 99% of $^{13}$C and marketed by MSD Isotop Co., Ltd., and added as an amount in terms of $^{13}$C-labelled formaldehyde.

TABLE 9

| Reaction mixture | |
|---|---|
| Reagent | Final concn. |
| H$^{13}$CHO | 50 mM |
| ribose 5-phosphate (Ri5P) | 75 mM |
| phosphoriboisomerase (PRI) | 10 U/ml |
| 3-hexulose phosphate synthase (HPS) | 5 U/ml |
| phosphohexuloisomerase (PHI) | 5 U/ml |
| phosphoglucoisomerase (PGI) | 5 U/ml |
| MgCl₂ | 5 mM |
| potassium phosphate buffer solution KPB (pH 7.5) | 50 mM | at 30° C.

EXAMPLE 3

Procedures of Example 1 were repeated except that a reaction mixture shown in Table 10 in place of the reaction mixture shown in Table 1 as in Example 1 was used with the results that 75 mM of $^{13}$C-labelled fructose 6-phosphate specifically labelled with $^{13}$C in a carbon position C-1 with an yield of 75% based on $^{13}$C-labelled formaldehyde (H$^{13}$CHO).

TABLE 10

| Reaction mixture | |
|---|---|
| Reagent | Final concn. |
| $^{13}$C-MeOH | 100 mM |
| ribose 5-phosphate (Ri5P) | 75 mM |
| alcohol oxidase (AOD) | 10 U/ml |
| phosphoriboisomerase (PRI) | 10 U/ml |
| 3-hexulose phosphate synthase (HPS) | 5 U/ml |
| phosphohexuloisomerase (PHI) | 5 U/ml |
| MgCl₂ | 5 mM |
| potassium phosphate buffer solution KPB (pH 7.5) | 50 mM | at 30° C.

EXAMPLE 4

Procedures of Example 1 were repeated except that a reaction mixture shown in Table 11 in place of the reaction mixture shown in Table 1 as in Example 1 was used with the results that 35 mM of $^{13}$C-labelled glucose 6-phosphate specifically labelled with $^{13}$C in a carbon position C-1 with an yield of 70% based on $^{13}$C-methanol, and 9 mM of $^{13}$C-labelled fructose 6-phosphate specifically labelled with $^{13}$C in a carbon position C-1 with an yield of 13% based on $^{13}$C-methanol. The catalase and hydrogen peroxide marketed by Sigma Biochemicals were used.

TABLE 11

| Reagent | Reaction mixture Final concn. or activity | |
|---|---|---|
| ribose 5-phosphate (Ri5P) | 75 mM | |
| alcohol oxidase (AOD) | 10 U/ml | |
| phosphoriboisomerase (PRI) | 10 U/ml | |
| 3-hexulose phosphate synthase (HPS) | 5 U/ml | |
| phosphohexuloisomerase (PHI) | 5 U/ml | |
| phosphoglucoisomerase (PGI) | 5 U/ml | |
| catalase | 200 U/ml | |
| MgCl$_2$ | 5 mM | |
| potassium phosphate buffer solution KPB (pH 7.5) | 50 mM | preincubation 5 min. at 30° C. |
| $^{13}$C-MeOH | 50 mM | |
| H$_2$O$_2$ | 150 mM | |

What is claimed is:

1. A process for preparing a $^{13}$C-labelled compound which comprises reacting a substrate and an aldehyde $^{13}$C-labelled carbon source compound at a C-1 position in the presence of an enzyme system consisting of lyase specific to the substrate belonging to EC4 group synthesizing a carbon-carbon bond and at least one of isomerases capable of isomerizing substrates to obtain a $^{13}$C-labelled compound specifically labelled with $^{13}$C, only in a carbon position C-1.

2. A process as claimed in claim 1, which process comprises reacting ribose 5-phosphate with $^{13}$C-labelled formaldehyde in the presence of a formaldehyde-fixing enzyme system consisting of phosphoriboisomerase, hexulose phosphate synthase and phosphohexuloisomerase to obtain $^{13}$C-labelled fructose 6-phosphate specifically with $^{13}$C, only in a carbon position C-1.

3. A process as claimed in claim 1, which process comprises reacting ribose 5-phosphate with $^{13}$C-labelled formaldehyde in the presence of a formaldehyde-fixing enzyme system consisting of phosphoriboisomerase, hexulose phosphate synthase, phosphohexuloisomerase and phosphoglucoisomerase to obtain $^{13}$C-labelled glucose 6-phosphate specifically with $^{13}$C, only in a carbon position C-1.

4. A process for preparing a $^{13}$C-labelled compound which comprises isomerizing a substrate in the presence of a first isomerase to form an isomerized substrate, reacting the isomerized substrate in the presence of lyase with an aldehyde $^{13}$C-labelled carbon source compound at a C-1 position to obtain a condensate specifically labelled with $^{13}$C, only in a carbon position C-1, and isomerizing the condensate in the presence of a second isomerase to obtain a first isomer specifically labelled with $^{13}$C, only in a carbon position C-1.

5. A process as claimed in claim 4, which process further comprises isomerizing the first isomer in the presence of a third isomerase to form a second isomer.

6. A process as claimed in claim 5, which process comprises isomerizing ribose 5-phosphate in the presence of phosphoriboisomerase to form riburose 5-phosphate, reacting the riburose 5-phosphate with $^{13}$C-labelled formaldehyde in the presence of hexulose phosphate synthase to form $^{13}$C-labelled hexulose 6-phosphate, isomerizing $^{13}$C-labelled hexulose 6-phosphate in the presence of phosphohexuloisomerase to form $^{13}$C-labelled fructose 6-phosphate, and isomerizing $^{13}$C-labelled fructose 6-phosphate in the presence of phosphoglucoisomerase to form $^{13}$C-labelled glucose 6-phosphate specifically labelled with $^{13}$C, only in a carbon position C-1.

7. A process as claimed in claim 4, which process comprises isomerizing ribose 5-phosphate in the presence of phosphoriboisomerase to form riburose 5-phosphate, reacting the riburose 5-phosphate with $^{13}$C-labelled formaldehyde in the presence of hexulose phosphate synthase to form $^{13}$C-labelled hexulose 6-phosphate, and isomerizing $^{13}$C-labelled hexulose 6-phosphate in the presence of phosphohexuloisomerase to form $^{13}$C-labelled fructose 6-phosphate specifically labelled with $^{13}$C, only in a carbon position C-1.

8. A process as claimed in any one of claims 6–7, wherein hexulose phosphate synthase and phosphohexuloisomerase are prepared by a process which comprises incubating and culturing *Methylomonas aminofaciens* 77a strain with a liquid medium containing methanol as a sole carbon source to obtain a cell-free extract, and separating and purifying the cell-free extract.

9. A process for preparing a $^{13}$C-labelled compound which process comprises reacting ribose 5-phosphate with $^{13}$C-labelled methanol in the presence of alcohol oxidase and of a formaldehyde-fixing enzyme system consisting of phosphoriboisomerase, hexulose phosphate synthase and phosphohexuloisomerase to obtain $^{13}$C-labelled fructose 6-phosphate specifically labelled with $^{13}$C, only in a carbon position C-1.

10. A process for preparing a $^{13}$C-labelled compound, which process comprises isomerizing ribose 5-phosphate in the presence of phosphoriboisomerae to form riburouse 5-phosphate, reacting the riburose 5-phosphate in the presence of hexulose phosphate synthase with $^{13}$C-labelled formaldehyde to form $^{13}$C-labelled hexulose 6-phosphate, and isomerizing $^{13}$C-labelled hexulose 6-phosphate in the presence of phosphohexuloisomerase to form $^{13}$C-labelled fructose 6-phosphate specifically labelled with $^{13}$C, only in a carbon position C-1, said $^{13}$C-labelled formaldehyde being formed by oxidizing $^{13}$C-labelled methanol in the presence of a alcohol oxidase.

11. A process for preparing a $^{13}$C-labelled compound, which process comprises reacting ribose 5-phosphate with $^{13}$C-labelled methanol in the presence of alcohol oxidase and of a formaldehyde-fixing enzyme system consisting of phosphoriboisomerase, hexulose phosphate synthase, phosphohexuloisomerase and phosphoglucoisomerase to obtain $^{13}$C-labelled glucose 6-phosphate specifically labelled with $^{13}$C, only in a carbon position C-1.

12. A process for preparing a $^{13}$C-labelled compound, which process comprises isomerizing ribose 5-phosphate in the presence of phosphoriboisomerase to form riburose 5-phosphate, reacting the riburose 5-phosphate in the presence of hexulose phosphate synthase with $^{13}$C-labelled formaldehyde to form $^{13}$C-labelled hexulose 6-phosphate, isomerizing $^{13}$C-labelled hexulose 6-phosphate in the presence of phosphohexuloisomerase to form $^{13}$C-labelled fructose 6-phosphate specifically labelled with $^{13}$C, only in a carbon position C-1, and isomerizing $^{13}$C-labelled fructose 6-phosphate in the presence of phosphoglucoisomerase to form $^{13}$C-labelled glucose 6-phosphate specifically labelled with $^{13}$C, only in a carbon position C-1, said $^{13}$C-labelled formaldehyde being formed by oxidizing $^{13}$C-labelled methanol in the presence of alcohol oxidase.

13. A process as claimed in claim 9, 10, 11, or 12 wherein said oxidase is used in combination with catalase and hydrogen peroxide.

14. A process as claimed in claim 2, 3, 9 or 11 wherein the formaldehyde-fixing enzyme system is a cell-free extract prepared by incubating and culturing *Methylomonas aminofaciens* 77a strain with a liquid medium containing methanol as a sole carbon source and containing phosphoriboisomerase, hexulose phosphate synthase, phosphohexuloisomerase and phosphoglucoisomerase.

* * * * *